United States Patent
Dumesic et al.

(10) Patent No.: US 9,242,952 B2
(45) Date of Patent: Jan. 26, 2016

(54) METHOD FOR SELECTIVELY PREPARING 5-HYDROXYMETHYLFURFUAL (HMF) FROM BIOMASS IN POLAR APROTIC SOLVENTS

(71) Applicant: Wisconsin Alumni Research Foundation, Madison, WI (US)

(72) Inventors: James A. Dumesic, Verona, WI (US); George W. Huber, Middleton, WI (US); Ronen Weingarten, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 14/229,481

(22) Filed: Mar. 28, 2014

(65) Prior Publication Data

US 2015/0274685 A1    Oct. 1, 2015

(51) Int. Cl.
*C07D 407/00* (2006.01)
*C07D 307/46* (2006.01)

(52) U.S. Cl.
CPC .................... *C07D 307/46* (2013.01)

(58) Field of Classification Search
CPC ............................ C07D 307/50; C07D 307/46
USPC ........................................................ 549/488
See application file for complete search history.

(56) References Cited

U.S. PATENT DOCUMENTS 8,314,267 B2    11/2012  Brandvold

OTHER PUBLICATIONS

Zhao et al Sci. Mag. vol. 316 (5831, pp. 1597-1600 Jun. 2007.*
Alamillo et al., The selective hydrogenation of biomass-derived 5-hydroxymethylfurfural using heterogeneous catalysts, *Green Chem.* 2012, 14, 1413-1419.
Alonso et al., Integrated conversion of hemicellulose and cellulose from lignocellulosic biomass, *Catalysis Science & Technology* 2013, 3, 927-931.
Alonso et al., Gamma-valerolactone, a sustainable platform molecule derived from lignocellulosic biomass, *Energy Environ. Sci.* 2013, 6, 76-80.
Alonso et al., Direct conversion of a cellulose to levulinic acid and gamma-valerolactone using solid acid catalysts, *Green Chem.* 2013, 15, 584-595.
Bicker et al., Dehydration of fructose to 5-hydroxymethylfurfural in sub- and supercritical acetone, *Green Chem.* 2003, 5, 280-284.
Bicker et al., Dehydration of D-fructose to hydroxymethylfurfural in sub- and supercritical fluids, *Journal of Supercritical Fluids* 2005, 36, 118-126.

(Continued)

*Primary Examiner* — Andrew D Kosar
*Assistant Examiner* — Raymond Covington
(74) *Attorney, Agent, or Firm* — Joseph T. Leone, Esq.; DeWitt Ross & Stevens S.C.

(57) ABSTRACT

A method to produce 5-hydroxymethylfurfural (HMF) is described in which a reactant including cellulose, lignocellulose, or a combination thereof, in a reaction mixture of a polar, aprotic solvent and an acid is reacted for a time, at a temperature, and at a hydrogen ion concentration wherein at least a portion of the cellulose or lignocellulose present in the reactant is converted to HMF. The reaction mixture is initially substantially devoid of water. As the reaction proceeds, dehydration of intermediates causes the water concentration in the reaction mixture to rise to no more than about 0.2 wt % water.

25 Claims, 10 Drawing Sheets

(56) References Cited

OTHER PUBLICATIONS

Binder et al., Simple chemical Transformation of Lignocellulosic Biomass into Furans for Fuels and Chemicals, *J. Am. Chem. Soc.* 2009, 131, 1979-1985.

Bond et al., Integrated Catalytic conversion of γ-Valerolactone to Liquid Alkanes for Transportation Fuels, *Science* 2010, 327, 1110-1114.

Cai et al., THF co-solvent enhances hydrocarbon and fuel precursor yields from lignocellulosic biomass, *Green Chem.* 2013.

Chheda et al., Production of 5-hydroxymethylfurfural and furfural by dehydration of biomass-derived mono- and poly-saccharides, *Green Chem.* 2007, 9, 342-350.

Daorattanachai et al., 5-Hydroxymethylfurfural production from sugars and cellulose in acid- and base-catalyzed conditions under hot compressed water, *Journal of Industrial and Engineering Chemistry* 2012, 18, 1893-1901.

Dutta et al., A Brief Summary of the Synthesis of Polyester Building-Block chemicals and Biofuels from 5-Hydroxymethylfurfural, *ChemPlusChem* 2012, 77, 259-272.

Gallo et al., Production and upgrading of 5-hydroxymethylfurfural using heterogeneous catalysts and biomass-derived solvents, *Green Chem.* 2013, 15, 85-90.

Gürbüz et al., Conversion of Hemicellulose into Furfural Using Solid Acid Catalysts in γ-Valerolactone, *Angewandte Chemie-International Edition* 2013, 52, 1270-1274.

Helle et al., A kinetic model for production of glucose by hydrolysis of levoglucosan and cellobiosan from pyrolysis oil, *Carbohydr. Res.* 2007, 342, 2365-2370.

Hu et al., Mediating acid-catalyzed conversion of levoglucosan into platform chemicals with various solvents, *Green Chem.* 2012, 14, 3087-3098.

Jae et al., Production of Dimethylfuran from Hydroxymethylfurfural through Catalytic Transfer Hydrogenation with Ruthenium Supported on Carbon, *ChemSusChem* 2013, 6, 1158-1162.

Kawamoto et al., Thermochemical conversion of cellulose in polar solvent (sulfolane) into levoglucosan and other low molecular-weight substances, *Journal of Analytical and Applied Pyrolysis* 2003, 70, 303-313.

Kelly et al., Single-Ion Solvation Free Energies and the Normal Hydrogen Electrode Potential in Methanol, Acetonitrile, and Dimethyl Sulfoxide, *J. Phys. Chem. B* 2007, 111, 408-422.

Kobayashi et al., High-Yielding One-Pot Synthesis of Glucose from Cellulose Using Simple Activated Carbons and Trace Hydrochloric Acid, *ACS Catalysis* 2013, 3, 581-587.

Li et al., Production of 5-hydroxymethylfurfural in ionic liquids under high fructose concentration conditions, *Carbohydr. Res.* 2010, 345, 1846-1850.

Lin et al., Kinetics and mechanism of Cellulose Pyrolysis, *J. Phys. Chem. C* 2009, 113, 20097-20107.

Liu et al., Dehydration of Highly concentrated Solutions of Fructose to 5-Hydroxymethylfurfural in a Cheap and sustainable Choline Chloride/Carbon dioxide System, *ChemSusChem* 2012, 5, 1223-1226.

Luterbacher et al., Nonenzymatic Sugar Production from Biomass Using Biomass-Derived γ-Valerolactone, *Science* 2014, 343, 277-280.

Ohara et al., Syntheses of 5-hydroxymethylfurfural and levoglucosan by selective dehydration of glucose using solid acid and base catalysts, *Applied Catalysis A: General* 2010, 383, 149-155.

Qi et al., Catalytic conversion of cellulose into 5-hydoxymethylfurfural in high yields via a two-step process, *Cellulose* 2011, 18, 1327-1333.

Rinaldi et al., Depolymerization of Cellulose Using Solid Catalysts in Ionic Liquids, *Angewandte Chemie-International Edition* 2008, 47, 8047-8050.

Rinaldi et al., Acid hydrolysis of Cellulose as the Entry Point into Biorefinery Schemes, *ChemSusChem* 2009, 2, 1096-1107.

Roman-Leshkov et al., Phase Modifiers Promote Efficient Production of Hydroxymethylfurfural from Fructose, *Science* 2006, 312, 1933-1937.

Roman-Leshkov et al., Production of dimethylfuran for liquid fuels from biomass-derived carbohydrates, *Nature* 2007, 447, 982-985.

Roman-Leshkov et al., Solvent Effects on Fructose Dehydration to 5-Hydroxymethylfurfural in Biphasic Systems Saturated with Inorganic Salts, *Topics in Catalysis* 2009, 52, 297-303.

Sen et al., conversion of biomass to sugars via ionic liquid hydrolysis: process synthesis and economic evaluation, *Biofuels, Bioproducts and Biorefining* 2012, 6, 444-452.

Shen et al., Hydrochloric Acid-Catalyzed levulinic Acid Formation from cellulose: Data and Kinetic Model to Maximize yields, *Aiche J.* 2012, 58, 236-246.

Su et al., single-step conversion of cellulose to 5-hydroxymethylfurfural *HMF), a versatile platform chemical, *Applied Catalysis A: General* 2009, 361, 117-122.

Tan et al., Ionic Liquids in Biomass Processing, in *Ionic Liquids*, vol. 290 (Ed.: B. Kirchner), Springer-Verlag Berlin, Berlin, 2009, pp. 311-339.

Van De Vyver et al., Catalytic production of levulinic acid from cellulose and other biomass-derived carbohydrates with sulfonated hyperbranched poly(arylene oxindole)s, *Energy Environ. Sci.* 2011, 4, 3601-3610.

Van Putten et al., Hydroxymethylfurfural, A Versatile Platform Chemical Made from Renewable Sources, *Chem. Rev.* 2013, 113, 1499-1597.

Vigier et al., Conversion of fructose and inulin to 5-hydroxymethylfurfural in sustainable betaine hydrochloride-based media, *Green Chem.* 2012, 14, 285-289.

Wang et al., Selective Production of Aromatics from Alkylfurans over Solid Acid Catalysts, *ChemCatChem* 2013, 5, 2044-2050.

Wettstein et al., Production of levulinic acid and gamma-valerolactone (GVL) from cellulose using GVL as a solvent in biphasic systems, *Energy Environ. Sci.* 2012, 5, 8199-8203.

Wettstein et al., RuSn bimetallic catalysts for selective hydrogenation of levulinic acid to γ-valerolactone, *Applied Catalysis B-Environmental* 2012, 117, 321-329.

Williams et al., Cycloaddition of Biomass-Derived Furans for Catalytic Production of Renewable p-Xylene, *ACS Catalysis* 2012, 2, 935-939.

Yang et al., Conversion of carbohydrates and lignocellulosic biomass into 5-hydroxymethylfurfural using $AlCl_3 \cdot 6H_2O$ catalyst in a biphasic solvent system, *Green Chem.* 2012, 14, 509-513.

Yin et al., Hydrothermal Conversion of Cellulose to 5-Hydroxymethyl Furfural, *Int. J. Green Energy* 2011, 8, 234-247.

Zakrzewska et al., Ionic Liquid-Mediated formation of 5-Hydroxymethylfurfural—A Promising Biomass-Derived Building Block, *Chem. Rev.* 2011, 111, 397-417.

Zhang et al., An Unexpected Reaction between 5-Hydroxymethylfurfural and Imadazolium-Based Ionic Liquids at high Temperatures, *Molecules* 2011, 16, 8463-8474.

Zhao et al., Metal Chlorides in Ionic Liquid solvents convert Sugars to 5-Hydroxymethylfurfural, *Science* 2007, 316, 1597-1600.

\* cited by examiner

METHOD FOR SELECTIVELY PREPARING 5-HYDROXYMETHYLFURFUAL (HMF) FROM BIOMASS IN POLAR APROTIC SOLVENTS

FEDERAL FUNDING STATEMENT

This invention was made with government support under DE-AC02-06CH11357 awarded by the US Department of Energy. The government has certain rights in the invention.

BACKGROUND

5-Hydroxymethyl furfural (HMF) is an alternative, non-petroleum precursor which can be used as a building block chemical for producing various high-volume and value-added organic chemicals. These chemicals include 2,5-furandicarboxylic acid (FDCA) which can serve as a precursor in the polymer industry[1], and 2,5-dimethylfuran (DMF) which can be used as a liquid transportation fuel.[2] DMF can also be used to produce p-xylene via cycloaddition with ethylene combined with dehydration over acidic zeolites and acidic oxides.[3] Alamillo et al. have shown quantitative yields of 2,5-di-hydroxy-methyl-tetrahydrofuran (DH-MTHF) from HMF with ruthenium-supported oxide catalysts.[4]

HMF is produced conventionally from glucose (in low yields) or fructose (in high yields) by a triple dehydration step with mineral acids in water.[5] It would be highly desirable to be able to produce HMF from cellulose, which is a more abundant and lower value feedstock than fructose. However, in aqueous systems, HMF is only produced in low yields (between 8 to 21%) from cellulose because of miscibility limitations and undesired formation of humins.[6] HMF production is maximized at relatively high temperatures (200-300° C.) and short reaction times (on the order of seconds or minutes). In aqueous systems, HMF is readily converted to formic acid and levulinic acid. The latter compound is also a versatile, bio-based platform chemical.[7]

The use of ionic liquids (ILs) as solvents for HMF production has been proposed due to the solvation capabilities of the ILs. A HMF yield of 51% from fructose was obtained by Li et al. when a high concentration of feed (67 wt %) was used in 1-butyl-3-methylimidazolium chloride.[8] Binder and Raines developed a process to convert lignocellulosic biomass to HMF using N,N-dimethylacetamide (DMA) containing lithium chloride as a solvent.[9] HMF yields of up to 54% were obtained with 1-ethyl-3-methylimidazolium chloride as an additive and a mixture of $CrCl_2$/HCl as the catalyst. Rinaldi et al. showed that solid acid catalysts can be used in 1-butyl-3-methylimidazolium chloride to selectively depolymerize cellulose to produce glucose and HMF.[10] Zhang and co-workers have reported HMF yields of 55% from cellulose with a mixture of $CuCl_2$ and $CrCl_2$ dissolved in 1-ethyl-3-methylimidazolium chlorid at relatively low temperatures.[11] A comprehensive review covering the process chemistry of HMF production from various feedstocks is given by van Putten et al.[12]

Significant challenges hinder the industrial use of ILs for production of HMF. Due to their high costs, quantitative recovery and recycling of ILs (at least 98%) is necessary to make the process economically attractive.[13] Relative low cellulose solubility (10-15 wt %) in ILs[14], high viscosity, and high toxicity of ILs are also impeding factors.[15] Thermal and chemical stabilities of ILs are also in question, as new compounds have been detected derived from side reactions between HMF and imidazolium-based ILs.[16] Extensive work has been reported by Jerome and co-workers to produce HMF from biomass derived feedstock in alternative solvent systems that are comparable with imidazolium-based ILs.[17] Alternative approaches have also been investigated using biphasic reaction systems with organic solvents that can extract the HMF from the aqueous phase before it undergoes further degradation reactions.[18] Phase modifiers (e.g., NaCl) can be added to the aqueous phase to help enhance HMF partitioning into the immiscible organic phase and consequently impede further HMF degradation.[19]

There thus remains a long-felt and unmet need for an easy, fast, and economical method to produce HMF from biomass.

SUMMARY OF THE INVENTION

Disclosed and claimed herein is a novel method to produce HMF from cellulosic biomass under mild reaction conditions in polar aprotic solvents (e.g., tetrahydrofuran) without the presence of water. Preferred reaction temperatures are in the range of from about 80° C. to about 300° C., more preferably from about 80° C. to about 250° C., more preferably still from about 80° C. to about 200° C., and most preferably from about 140° C. to about 190° C. The reaction conditions are preferably mildly to very mildly acidic. Preferably $[H^+] \leq$ about 500 mM, more preferably $[H^+] \leq$ about 100 mM, more preferably still $[H^+] \leq$ about 50 mM. Preferred acidities are from about 5 mM $[H^+]$ to about 50 mM $[H^+]$. The acidity can be provided by any suitable acid, such as mineral acid (e.g., HCl, $HNO_3$, $H_2SO_4$, and the like.) In this system, levoglucosan is the major decomposition product of cellulose found in the biomass. The levoglucosan is then dehydrated to yield HMF. Glucose, levulinic acid and formic acid are also produced as a result of side reactions with water which is formed as a by-product of the levoglucosan dehydration reaction. The turnover frequency for cellulose conversion increases as the water content in the solvent decreases, with conversion rates in THF being more than twenty times higher than those in water. Thus, it is preferred that the initial reaction solvent be substantially water-free. As shown in the Examples, the highest HMF yield from cellulose was 44% and the highest combined yield of HMF and levulinic from cellulose was 53%, which are comparable to yields obtained in ionic liquids or biphasic systems. Moreover, the use of a low boiling point, aprotic polar solvent, such as THF, facilitates recovery of HMF in downstream processes.

Thus, disclosed herein is a method to produce 5-hydroxymethylfurfural (HMF) from cellulosic biomass. The method comprises reacting a reactant comprising cellulose, lignocellulose, or a combination thereof, in a reaction mixture comprising a polar, aprotic solvent and an acid, and wherein the reaction mixture is initially substantially devoid of water, for a time, at a temperature, and at a hydrogen ion concentration wherein at least a portion of the cellulose or lignocellulose present in the reactant is converted to HMF.

Preferably, the acid is present in an amount to yield a hydrogen ion concentration in the reaction mixture of from about 5 mM to about 500 mM, or from about 5 mM to about 100 mM, or from about 5 mM to about 50 mM. The acid may be a Brønsted-Lowry acid, although this is not required. The acid may be a Lewis acid. Mineral acids are most preferred.

The reaction may be carried out at any suitable temperature. However, it is preferred that the reaction temperature is from about 120° C. to about 300° C., or from about 120° C. to about 250° C., or from about 120° C. to about 200° C., or from about 140° C. to about 190° C.

Any polar, aprotic solvent may be used in the method. Such solvents include, for example (and not by way of limitation), beta-, gamma-, and delta-lactones, hydrofurans, hydropyrans, and combinations thereof. The polar, aprotic solvent may be selected from the group consisting of dichloromethane, tetrahydrofuran, ethylacetate, acetone, dimethylformamide, acetonitrile, dimethylsulfoxide, propylene carbonate, N-methyl-2-pyrrolidone, and hexamethylphosphoramide.

In a second version of the method, the reaction mixture comprises no more than about 0.2 wt % water at any time during the reaction. All of the other considerations noted above for acid type, hydrogen ion concentration, solvent type, etc. apply to this version of the invention as well. Thus, the method explicitly includes reacting a reactant comprising cellulose, lignocellulose, or a combination thereof, in a reaction mixture comprising a polar, aprotic solvent and an acid, for a time, at a temperature, and at a hydrogen ion concentration wherein at least a portion of the cellulose or lignocellulose present in the reactant is converted to HMF; wherein the reaction mixture is initially substantially devoid of water; and wherein the reaction mixture comprises no more than about 0.2 wt % water at any time during the reaction.

In the second version of the method, the acid is preferably present in an amount to yield a hydrogen ion concentration in the reaction mixture of from about 5 mM to about 500 mM, or from about 5 mM to about 100 mM, or from about 5 mM to about 50 mM. The acid may be a Brønsted-Lowry acid, although this is not required. The acid may be a Lewis acid. Mineral acids are most preferred.

In the second version of the method, the reaction may be carried out at any suitable temperature. However, it is preferred that the reaction temperature is from about 120° C. to about 300° C., or from about 120° C. to about 250° C., or from about 120° C. to about 200° C., or from about 140° C. to about 190° C.

Any polar, aprotic solvent may be used in the second version of the method method. Such solvents include, for example (and not by way of limitation), beta-, gamma-, and delta-lactones, hydrofurans, hydropyrans, and combinations thereof. The polar, aprotic solvent may be selected from the group consisting of dichloromethane, tetrahydrofuran, ethylacetate, acetone, dimethylformamide, acetonitrile, dimethylsulfoxide, propylene carbonate, N-methyl-2-pyrrolidone, and hexamethylphosphoramide.

BRIEF DESCRIPTION OF THE DRAWINGS

FIG. 3A: levoglucosan. FIG. 3B: glucose. FIG. 3C: HMF. FIG. 3D: levulinic acid. Cellulose loading was 5 wt % and reaction volume was 60 mL. Catalyst concentration was 5 mM sulfuric acid; water (■), water:THF 1:1 v/v (●), Water:THF 1:9 v/v (▲), THF (★).

FIG. 4A depicts carbon yield of detectable products. FIG. 4B depicts relative carbon selectivity of detectable products. Cellulose loading was 1 wt % and reaction volume was 60 mL. Catalyst concentration was 5 mM sulfuric acid. Levoglucosan (■); glucose (▨); HMF (□); furfural (▩); levulinic acid (◩); formic acid (◪).

FIG. 5A: Total detectable products. FIG. 5B: HMF. FIG. 5C: levulinic acid. Feedstock loading was 2 wt % and reaction volume was 60 mL. Catalyst concentration was 5 mM sulfuric acid.

FIG. 7A: Total detectable products. FIG. 7B: levoglucosan. FIG. 7C: HMF. FIG. 7D: levulinic acid. Feedstock loading was 2 wt % and reaction volume was 60 mL. Catalyst concentration was 5 mM sulfuric acid. Water (■), THF (●).

FIG. 10A: levoglucosan. FIG. 10B: glucose. FIG. 10C: HMF. FIG. 10D: levulinic acid. Cellulose loading was 1 wt % and reaction volume was 60 mL. Catalyst concentration was 5 mM sulfuric acid. T/° C.=140 (■), 170 (●), 190 (▲), 210 (★).

DETAILED DESCRIPTION

Figure 1:
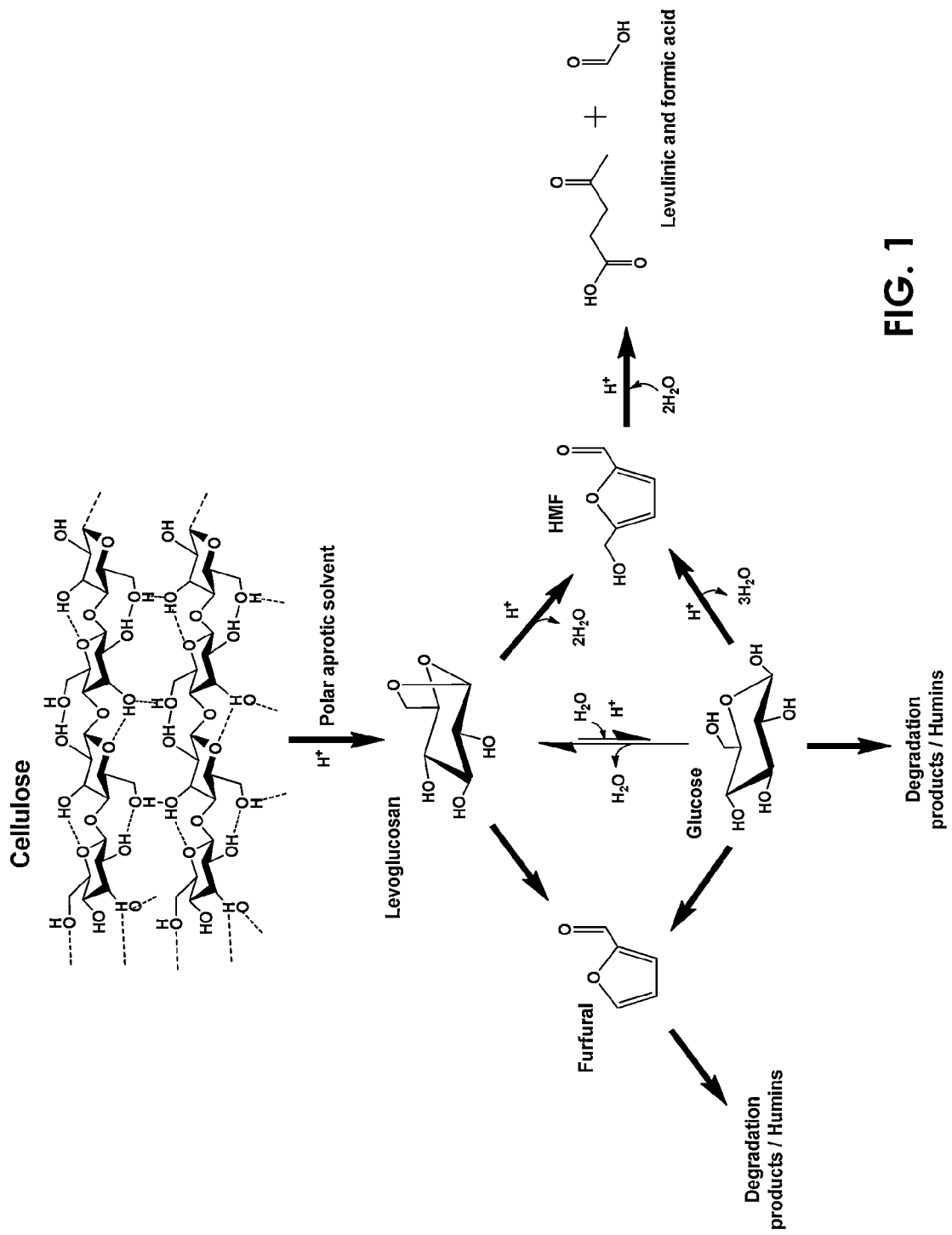
FIG. 1 depicts a proposed reaction scheme for HMF production from cellulose in polar aprotic solvents under acidic conditions.

Abbreviations and Definitions:

DHMTHF=2,5-di-hydroxy-methyl-tetrahydrofuran. DMA=N,N-dimethylacetamide. DMF=2,5-dimethylfuran. FA=formic acid. FDCA=2,5-furandicarboxylic acid. Fur=furfural. GVL=gamma-valerolactone. HMF=5-hydroxymethyl furfural. IL=ionic liquid. LA=levulinic acid. THF=tetrahydrofuran. TOF=turnover frequency.

"Biomass" as used herein includes materials containing cellulose, hemicellulose, lignin, protein and carbohydrates such as starch and sugar. Common forms of biomass include trees, shrubs and grasses, corn and corn husks as well as municipal solid waste, waste paper and yard waste. Biomass high in starch, sugar or protein such as corn, grains, fruits and vegetables, is usually consumed as food. Conversely, biomass high in cellulose, hemicellulose and lignin is not readily digestible by humans and is primarily utilized for wood and paper products, fuel, or is discarded as waste. "Biomass" as used herein explicitly includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods. In addition, biomass includes organic waste materials generated from agricultural processes including farming and forestry activities, specifically including forestry wood waste. "Biomass" includes virgin biomass and/or non-virgin biomass such as agricultural biomass, commercial organics, construction and demolition debris, municipal solid waste, waste paper, and yard waste. Municipal solid waste generally includes garbage, trash, rubbish, refuse and offal that is normally disposed of by the occupants of residential dwelling units and by business, industrial and commercial establishments, including but not limited to: paper and cardboard, plastics, food scraps, scrap wood, saw dust, and the like.

"Biomass-derived"=Compounds or compositions fabricated or purified from biomass. Glucose for use in the disclosed method may be biomass-derived.

"Brønsted-Lowry Acid/Base"=A Brønsted-Lowry acid is defined herein as any chemical species (atom, ion, molecule, compound, complex, etc.), without limitation, that can donate or transfer one or more protons to another chemical species. Mono-protic, diprotic, and triprotic acids are explicitly included within the definition. A Brønsted-Lowry base is defined herein as any chemical species that can accept a proton from another chemical species. Included among Brønsted-Lowry acids are mineral acids, organic acids, heteropolyacids, solid acid catalysts, zeolites, etc. as defined herein. Note that this list is exemplary, not exclusive. The shortened term "Brønsted" is also used synonymously with "Brønsted-Lowry."

"Carbohydrate" is defined herein as a compound that consists only of carbon, hydrogen, and oxygen atoms, in any ratio.

"$C_5$ carbohydrate" refers to any carbohydrate, without limitation, that has five (5) carbon atoms. The definition includes pentose sugars of any description and stereoisomerism (e.g., D/L aldopentoses and D/L ketopentoses). $C_5$ carbohydrates include (by way of example and not limitation) arabinose, lyxose, ribose, ribulose, xylose, and xylulose.

"$C_6$ carbohydrate" refers to any carbohydrate, without limitation, that has six (6) carbon atoms. The definition includes hexose sugars of any description and stereoisomerism (e.g., D/L aldohexoses and D/L ketohexoses). $C_6$ carbohydrates include (by way of example and not limitation) allose, altrose, fructose, galactose, glucose, gulose, idose, mannose, psicose, sorbose, tagatose, and talose.

"Cellulose" refers to a polysaccharide of glucose monomers (($C_6H_{10}O_5)_n$); "cellulosic biomass" refers to biomass as described earlier that comprises cellulose, and/or consists essentially of cellulose, and/or consists entirely of cellulose. Lignocellulosic biomass refers to biomass comprising cellulose, hemicellulose, and lignin. Lignocellulosic biomass comprises xylose, as does hemicellulose.

"Glucose-containing oligomers, glucose-containing polymers, Glucose-containing reactant, C6-containing reactant"=Any chemical species, having any type of intramolecular bond type, that comprises a glucose unit. The definition explicitly includes glucose-containing disaccharides (such as, but not limited to, sucrose, lactose, maltose, trehalose, cellobiose, kojibiose, nigerose, isomaltose, β,β-trehalose, α,β-trehalose, sophorose, laminaribiose, gentiobiose, turanose, maltulose, palatinose, gentiobiulose, etc.), trisaccharides (such as, but not limited to, isomaltotriose, nigerotriose, maltotriose, maltotriulose, raffinose, etc.), and larger oligosaccharides and polysaccharides, as well as large and more complex glucose-containing polymers and carbohydrates, such as, but not limited to, starch, amylase, amylopectin, glycogen, cellulose, hemicelluloses (e.g., xyloglucan, glucomannan, etc.), lignocellulose, and the like. Linear, branched, and macrocyclic oligomers and polymers containing glucose are explicitly included within the definition.

"Homogeneous catalyst"=A catalyst that exists in the same phase (solid, liquid, or gas) as the reactants under reaction conditions. "Heterogeneous catalyst"=A catalyst that exists in a different phase than the reactants under reaction conditions.

"Hydrofuran" is used herein to refer to any unsubstituted or substituted cyclic ether having a single oxygen heteroatom in the ring, and having five total atoms in the ring and which is derived from furanic compounds. Hydrofurans that are miscible in water, such as tetrahydrofuran (THF), are more appropriate for use in the monophasic reactions described herein.

"Hydropyran" is used herein to refer to any unsubstituted or substituted cyclic ether having a single oxygen heteroatom in the ring, and having six total atoms in the ring and which is derived from pyranic compounds. Hydropyrans miscible in water are more appropriate for use in the monophasic reactions described herein.

"Lactone" as used herein refers to an unsubstituted or substituted cyclic ester, having a single oxygen heteroatom in the ring, and having from four to six total atoms in the ring—i.e., beta, gamma, and delta lactones, derived from any corresponding C4 to C16 carboxylic acid. Thus, as used herein, the term "lactone" explicitly includes (without limitation) unsubstituted and substituted beta and gamma-butyrolactone and beta-, gamma-, and delta-valerolactones to beta-, gamma, and delta-hexadecalactones. Some lactones are miscible in water, such as GVL; other lactones have more limited solubility in water.

"Lewis Acid/Base"=A Lewis acid is defined herein as any chemical species that is an electron-pair acceptor, i.e., any chemical species that is capable of receiving an electron pair, without limitation. A Lewis base is defined herein as any chemical species that is an electron-pair donor, that is, any chemical species that is capable of donating an electron pair, without limitation.

The Lewis acid (also referred to as the Lewis acid catalyst) may be any Lewis acid based on transition metals, lathanoid metals, and metals from Group 4, 5, 13, 14 and 15 of the periodic table of the elements, including boron, aluminum, gallium, indium, titanium, zirconium, tin, vanadium, arsenic, antimony, bismuth, lanthanum, dysprosium, and ytterbium. One skilled in the art will recognize that some elements are better suited in the practice of the method. Illustrative examples include $AlCl_3$, (alkyl)$AlCl_2$, $(C_2H_5)_2AlCl$, $(C_2H_5)_3Al_2Cl_3$, $BF_3$, $SnCl_4$ and $TiCl_4$.

The Group 4, 5 and 14 Lewis acids generally are designated by the formula $MX_4$; wherein M is Group 4, 5, or 14 metal, and X is a halogen independently selected from the group consisting of fluorine, chlorine, bromine, and iodine, preferably chlorine. X may also be a psuedohalogen. Non-limiting examples include titanium tetrachloride, titanium tetrabromide, vanadium tetrachloride, tin tetrachloride and zirconium tetrachloride. The Group 4, 5, or 14 Lewis acids may also contain more than one type of halogen. Non-limiting examples include titanium bromide trichloride, titanium dibromide dichloride, vanadium bromide trichloride, and tin chloride trifluoride.

Group 4, 5 and 14 Lewis acids useful in the method may also have the general formula $MR_nX_{4-n}$; wherein M is Group 4, 5, or 14 metal; wherein R is a monovalent hydrocarbon radical selected from the group consisting of $C_1$ to $C_{12}$ alkyl, aryl, arylalkyl, alkylaryl and cycloalkyl radicals; wherein n is an integer from 0 to 4; and wherein X is a halogen independently selected from the group consisting of fluorine, chlorine, bromine, and iodine, preferably chlorine. X may also be a psuedohalogen. Non-limiting examples include benzyltitanium trichloride, dibenzyltitanium dichloride, benzylzirconium trichloride, dibenzylzirconium dibromide, methyltitanium trichloride, dimethyltitanium difluoride, dimethyltin dichloride and phenylvanadium trichloride.

Group 4, 5 and 14 Lewis acids useful in method may also have the general formula $M(RO)_nR'_mX_{(m+n)}$; wherein M is Group 4, 5, or 14 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is an integer from 0 to 4; m is an integer from 0 to 4 such that the sum of n and m is not more than 4; and X is a halogen independently selected from the group consisting of fluorine, chlorine, bromine, and iodine, preferably chlorine. X may also be a psuedohalogen. Non-limiting examples include methoxytitanium trichloride, n-butoxytitanium trichloride, di(isopropoxy)titanium dichloride, phenoxytitanium tribromide, phenylmethoxyzirconium trifluoride, methyl methoxytitanium dichloride, methyl methoxytin dichloride and benzyl isopropoxyvanadium dichloride.

Group 5 Lewis acids may also have the general formula $MOX_3$; wherein M is a Group 5 metal; X is a halogen independently selected from the group consisting of fluorine, chlorine, bromine, and iodine, preferably chlorine. A non-limiting example is vanadium oxytrichloride.

The Group 13 Lewis acids have the general formula $MX_3$; wherein M is a Group 13 metal and X is a halogen independently selected from the group consisting of fluorine, chlorine, bromine, and iodine, preferably chlorine. X may also be a psuedohalogen. Non-limiting examples include aluminum trichloride, boron trifluoride, gallium trichloride, indium trifluoride, and the like.

The Group 13 Lewis acids useful in method may also have the general formula: $MR_nX_{3-n}$ wherein M is a Group 13 metal; R is a monovalent hydrocarbon radical selected from the group consisting of $C_1$ to $C_{12}$ alkyl, aryl, arylalkyl, alkylaryl and cycloalkyl radicals; and n is an number from 0 to 3; and X is a halogen independently selected from the group consisting of fluorine, chlorine, bromine, and iodine, preferably chlorine. X may also be a psuedohalogen. Non-limiting examples include ethylaluminum dichloride, methylaluminum dichloride, benzylaluminum dichloride, isobutylgallium dichloride, diethylaluminum chloride, dimethylaluminum chloride, ethylaluminum sesquichloride, methylaluminum sesquichloride, trimethylaluminum and triethylaluminum.

Group 13 Lewis acids useful in this disclosure may also have the general formula $M(RO)_nR'_mX_{3-(m+n)}$; wherein M is a Group 13 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3; m is an number from 0 to 3 such that the sum of n and m is not more than 3; and X is a halogen independently selected from the group consisting of fluorine, chlorine, bromine, and iodine, preferably chlorine. X may also be a psuedohalogen. Non-limiting examples include methoxyaluminum dichloride, ethoxyaluminum dichloride, 2,6-di-tert-butylphenoxyaluminum dichloride, methoxy methylaluminum chloride, 2,6-di-tert-butylphenoxy methylaluminum chloride, isopropoxygallium dichloride and phenoxy methylindium fluoride.

Group 13 Lewis acids useful in this disclosure may also have the general formula $M(RC(O)O)_nR'_mX_{3-(m+n)}$; wherein M is a Group 13 metal; RC(O)O is a monovalent hydrocarbacyl radical selected from the group consisting of $C_2$ to $C_{30}$ alkacyloxy, arylacyloxy, arylalkylacyloxy, alkylarylacyloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3 and m is a number from 0 to 3 such that the sum of n and m is not more than 3; and X is a halogen independently selected from the group consisting of fluorine, chlorine, bromine, and iodine, preferably chlorine. X may also be a psuedohalogen. Non-limiting examples include acetoxyaluminum dichloride, benzoyloxyaluminum dibromide, benzoyloxygallium difluoride, methyl acetoxyaluminum chloride, and isopropoyloxyindium trichloride.

The most preferred Lewis acids for use in the method are metal halides generally and more specifically transition metal halides, lathanoid metal halides, and Group 5, 13, and 14 metal halides. Preferred among the metal halides are metal chlorides. Preferred transition metal chlorides include, but are not limited to, $TiCl_4$, $VCl_3$ and the like. Preferred Group 13 and 14 metal halides and chlorides include, but are not limited to, $BF_3$, $AlCl_3$, $SnCl_4$, $InCl_3$, and $GaCl_3$. Preferred lanthanoid chlorides include, but are not limited to, $LaCl_3$, $DyCl_3$ and $YbCl_3$.

The terms "solid acid" and "solid acid catalyst" are used synonymously herein and can comprise one or more solid acid materials. The solid acid catalyst can be used independently or alternatively can be utilized in combination with one or more mineral acid or other types of catalysts. Exemplary solid acid catalysts which can be utilized include, but are not limited to, heteropolyacids, acid resin-type catalysts, mesoporous silicas, silica-alumina, acid clays, sulfated zirconia, phosphates such as zirconium phosphate, molecular sieve materials, zeolites, and acidic material on a thermally stable support. Where an acidic material is provided on a thermally stable support, the thermo-stable support can include for example, one or more of silica, tin oxide, niobia, zirconia, titania, carbon, alpha-alumina, and the like. The oxides themselves (e.g., $ZrO_2$, $SnO_2$, $TiO_2$, etc.) which may optionally be doped with additional acid groups such as $SO_4^{2-}$ or $SO_3H$ may also be used as solid acid catalysts.

Further examples of solid acid catalysts include strongly acidic ion exchangers such as cross-linked polystyrene containing sulfonic acid groups. For example, the Amberlyst®-brand resins are functionalized styrene-divinylbenzene copolymers with different surface properties and porosities. (These types of resins are designated herein as "Amb" resins, followed by a numeric identifier of the specific sub-type of resin where appropriate.) The functional group is generally of the sulfonic acid type. The Amberlyst®-brand resins are supplied as gellular or macro-reticular spherical beads. (Amberlyst® is a registered trademark of the Dow Chemical Co.) Similarly, Nafion®-brand resins are sulfonated tetrafluoroethylene-based fluoropolymer-copolymers which are solid acid catalysts. Nafion® is a registered trademark of E.I. du Pont de Nemours & Co.)

Solid catalysts can be in any shape or form now known or developed in the future, such as, but not limited to, granules, powder, beads, pills, pellets, flakes, cylinders, spheres, or other shapes.

Zeolites may also be used as solid acid catalysts. Of these, H-type zeolites are generally preferred, for example zeolites in the mordenite group or fine-pored zeolites such as zeolites X, Y and L, e.g., mordenite, erionite, chabazite, or faujasite. Also suitable are ultrastable zeolites in the faujasite group which have been dealuminated.

Total Carbon Yield:

Tot. C Yield (%) =

$$100 \times \frac{\text{total moles of carbon from all detectable products}^*}{\text{initial moles of carbon in feed}}$$

*Detectable products: glucose, levoglucosan, FA, LA, HMF, Fur.

Relative Carbon Selectivity (%):

[Relative carbon selectivity]$_i$(%) =

$$100 \times \frac{\text{moles of carbon of product } i}{\text{total moles of carbon from all detectable products}}$$

Carbon Yield:

$$[\text{Carbon yield}]_i(\%) = 100 \times \frac{\text{moles of carbon of product } i}{\text{initial moles of carbon in feed}}$$

Turnover Frequency:

Turnover frequency (hr$^{-1}$) =

$$\frac{d(\text{total moles of carbon produced})}{dt} \times \frac{1}{\text{moles of protons}}$$

"Mineral acid"=an acid derived from one or more inorganic compounds. Examples include, but are not limited to hydrochloric acid (HCl), nitric acid (HNO$_3$), phosphoric acid (H$_3$PO$_4$), sulfuric acid (H$_2$SO$_4$) boric acid (H$_3$BO$_3$), hydrofluoric acid (HF), hydrobromic acid (HBr), perchloric acid (HClO$_4$), and the like.

"Polar, aprotic solvent"=Any solvent having a net positive dipole moment, a relatively high dielectric constant, and which lacks a labile (acidic) hydrogen atom. Examples of polar, aprotic solvents include, but are not limited to, dichloromethane, hydrofurans (e.g. tetrahydrofuran), hydropyrans, ethylacetate, acetone, dimethylformamide, acetonitrile, dimethylsulfoxide, propylene carbonate, N-methyl-2-pyrrolidone, hexamethylphosphoramide, and the like.

"Substantially devoid of" means that the listed item, ingredient, or reagent is present in an amount of from 0 wt % to no more than 0.5 wt % of the total composition.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations shall include the corresponding plural characteristic or limitation, and vice-versa, unless otherwise specified or clearly implied to the contrary by the context in which the reference is made.

The processes described herein can be run in batch mode, semi-continuous mode, and/or continuous mode, all of which are explicitly included herein.

All combinations of method or process steps as used herein can be performed in any order, unless otherwise specified or clearly implied to the contrary by the context in which the referenced combination is made.

The methods described and claimed herein can comprise, consist of, or consist essentially of the essential elements and limitations of the disclosed methods, as well as any additional or optional ingredients, components, or limitations described herein or otherwise useful in synthetic organic chemistry.

Overview:

Disclosed herein is a method to produce HMF from cellulose-containing biomass in polar aprotic solvents in the substantial absence of water as a co-solvent. The method is able to produce HMF from cellulosic biomass in yields that approach those obtained in ILs or biphasic systems).[20] Moreover, HMF and other reaction byproducts can be separated from the polar aprotic solvent using conventional separation technologies like distillation and evaporation (by way of example and not limitation). The method runs contrary previous perceptions of liquid phase cellulose decomposition wherein the presence of water has been thought to be necessary to convert cellulose into HMF via a hydrolysis route.[21]

FIG. 1 shows the proposed reaction pathway to produce HMF from cellulose in polar aprotic solvents. (Note that the claimed method is not limited to any specific underlying mechanism. The reaction pathway shown in FIG. 1 is a proposed reaction pathway, i.e., a plausible pathway that accounts for the observed products.) As shown in FIG. 1, it is proposed that cellulose initially undergoes reaction to produce levoglucosan under dilute acidic conditions at temperatures in the range of from about 140 to about 190° C. It has been reported that levoglucosan can be produced from cellulose in the organic solvent sulfolane, but that relatively higher temperatures (200-330° C.) were required to carry out the reaction and a catalyst was not used.[22] The Examples contained herein suggest that acid is necessary to produce levoglucosan as confirmed by blank studies (without acid catalyst) with cellulose in THF. The reactions conducted without acid resulted in negligible cellulose conversion (no detectable products) at 170° C. after 6 hours.

The levoglucosan then undergoes a double dehydration step to produce HMF. Again, see FIG. 1. The water produced in this reaction can react with levoglucosan to produce glucose.[23] HMF can also undergo rehydration with water over an acid catalyst to produce levulinic acid (LA) and formic acid (FA). Once glucose is formed, it can also undergo dehydration to produce HMF, as well as undergo degradation to produce degradation products (i.e., humins). Furfural (Fur) was also detected in carbon yields lower than 4%. It has been reported that furfural is a by-product of levoglucosan and/or glucose[25] decomposition. Separate decomposition studies with HMF in THF and sulfuric acid showed that HMF is stable in the non-aqueous environment with conversions below 3% at 190° C. after 120 minutes. Other studies have also mentioned that THF prevents further degradation of furfural and HMF.[26]

Figure 2:
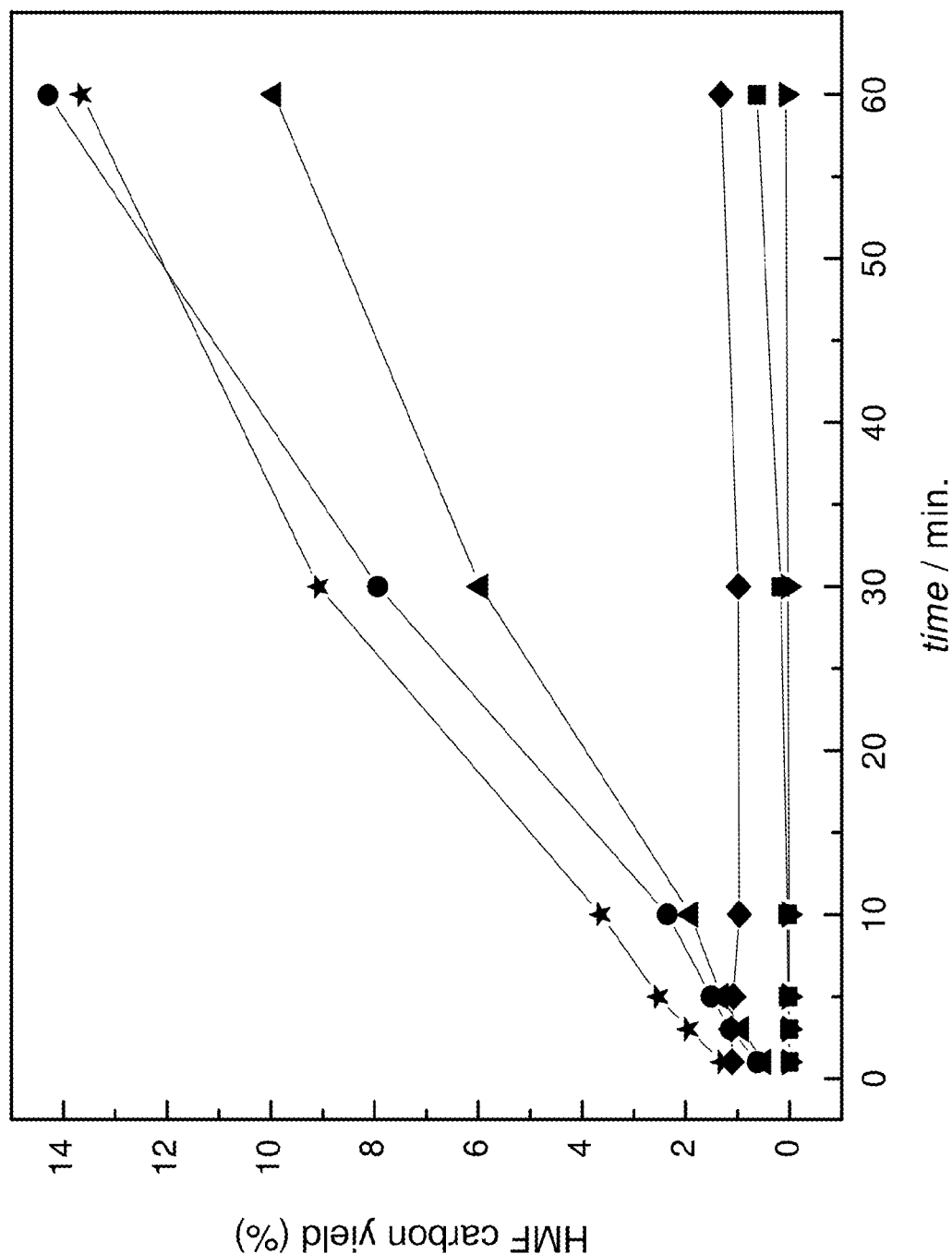
FIG. 2 is a graph depicting cellulose decomposition and HMF production as a function of reaction time at 170° C. in polar protic and aprotic solvents under acidic conditions. Cellulose loading was 5 wt % and solvent volume was 60 mL. Catalyst concentration was 5 mM sulfuric acid; water (■); THF (●); GVL (▲); ethyl acetate (◆); acetone (★); ethanol (▼).

The polar aprotic solvents including γ-valerolactone (GVL), acetone and tetrahydrofuran (THF) showed considerably higher yields of HMF from cellulose as compared to HMF yields in ethyl acetate, water and ethanol, as shown in FIG. 2. The HMF yield increased in the following order: ethanol<water<ethyl acetate<<GVL<acetone ~THF. Reactions in water and ethanol, both protic solvents, resulted in the lowest HMF yields. Despite being a polar aprotic solvent, the yields obtained in ethyl acetate were only somewhat higher compared to the protic solvents. It is hypothesized that this behavior is due to the instability of ethyl acetate under the applied reaction conditions where water (from the dehydration reaction) reacts with ethyl acetate to form ethanol and acetic acid. Both of these by-products were detected with HPLC when ethyl acetate was used as a solvent. Acetone has been shown to be a valuable solvent for HMF production from carbohydrates.[27] However, acetone is not stable under acidic conditions; it undergoes aldol-type reactions to form dimers and trimers.[27a]

Previous work has shown GVL to be a diverse renewable chemical for biomass processing.[28] Alonso et al. used a monophasic system comprised of a solution of 90 wt % GVL and 10 wt % water as the solvent with Amberlyst 70 to selectively produce levulinic acid from cellulose with yields close to 70%.[29] Increasing the amount of water in the solvent decreased the reaction rate. GVL/water solutions were also used to convert the hemicellulose and cellulose fractions of lignocellulosic biomass to furfural and levulinic acid respectively.[25,30] However, it has also been reported that GVL undergoes oxidation to form degradation products in the presence of molecular oxygen.[31]

Figures 3A, 3B, 3C, 3D:
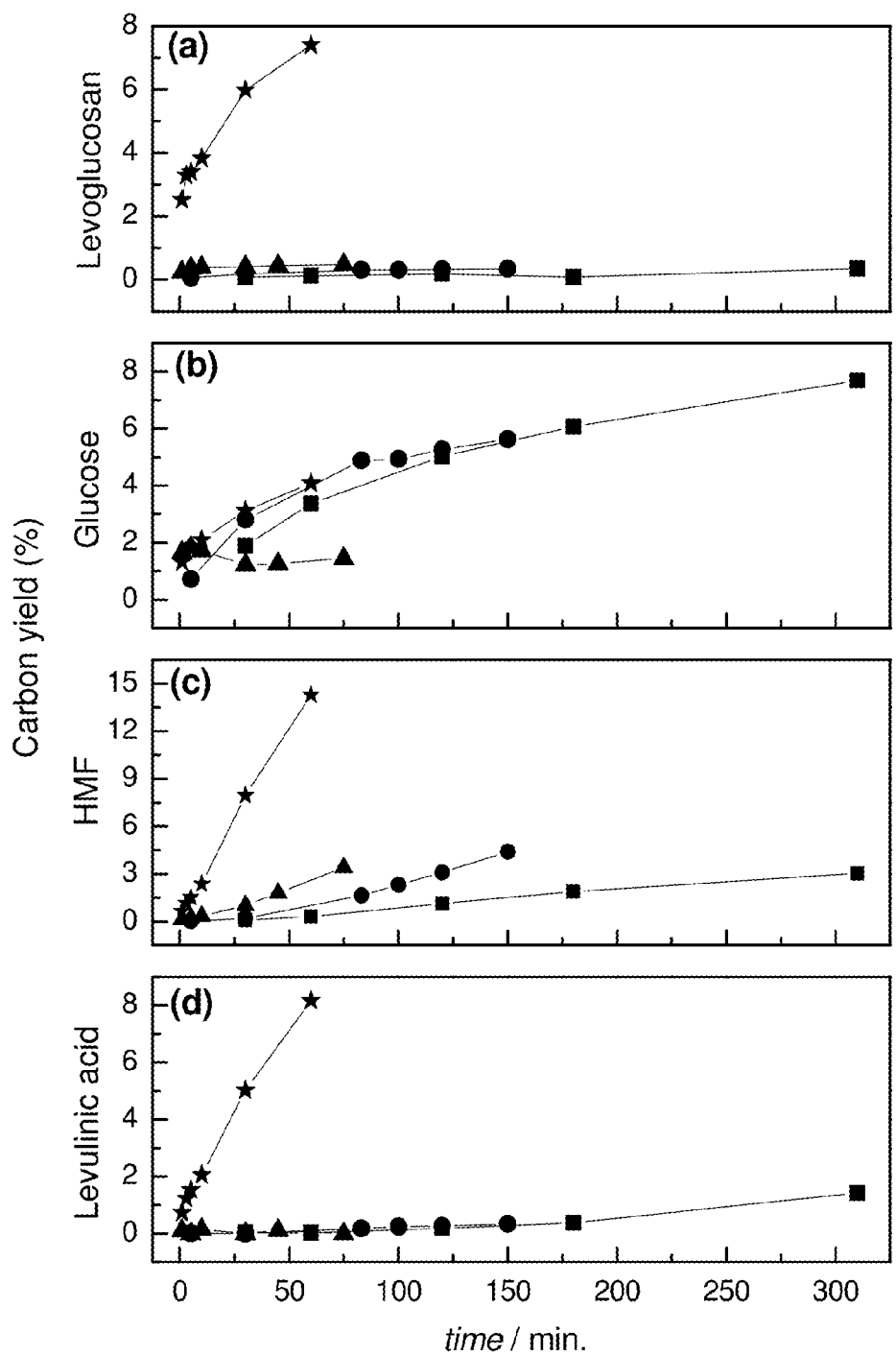
FIGS. 3A, 3B, 3C, and 3D are a series of graphs depicting cellulose decomposition as a function of solvent composition (THF/water mixtures) under acidic conditions. In each figure, the carbon yield of a major product as a function of reaction time at 170° C. is given.
Figures 5A, 5B, 5C:
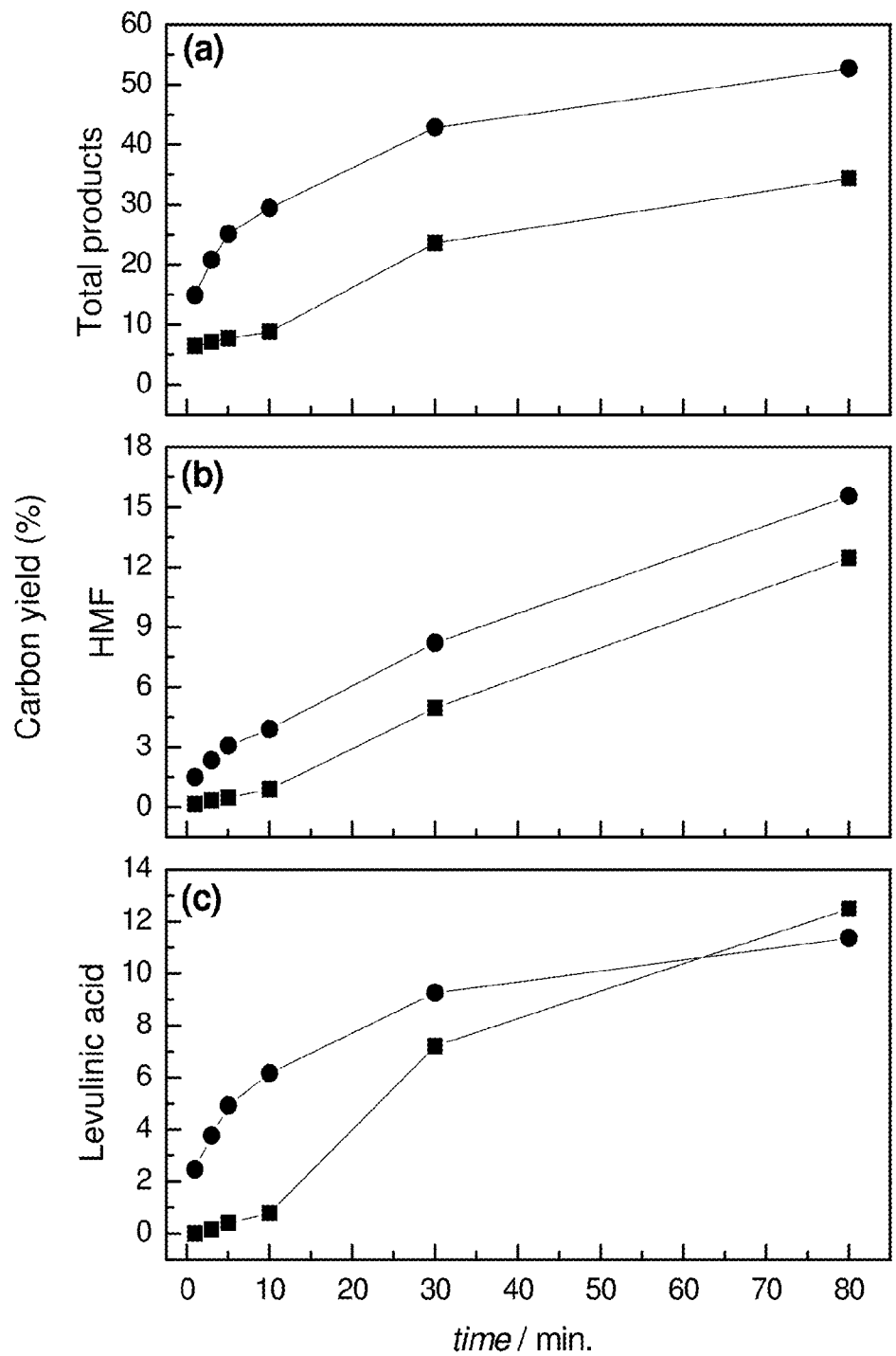
FIGS. 5A, 5B, and 5C are a series of graphs depicting the results of dehydration studies in THF with levoglucosan (■) and glucose (●) feedstocks under acidic conditions at 170° C. Carbon yields are presented as a function of reaction time.
Figure 6:
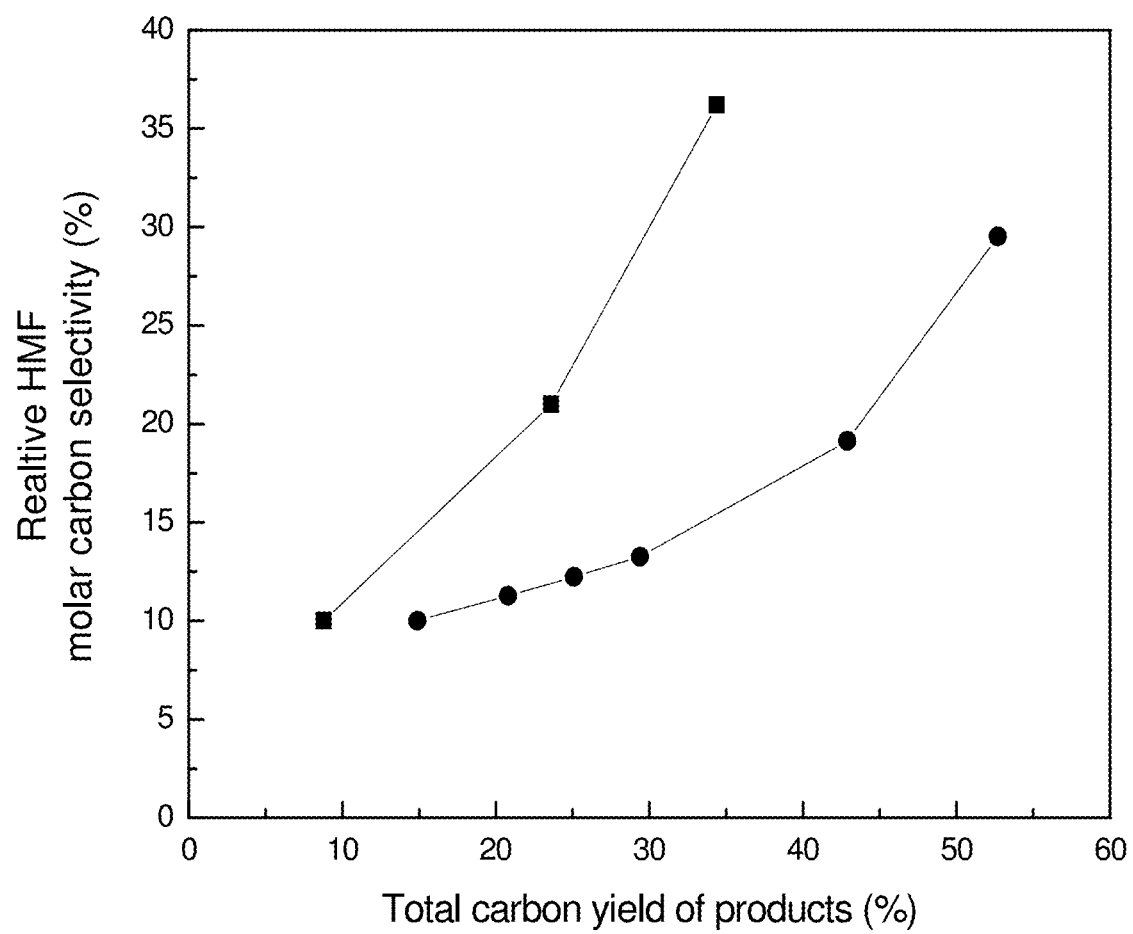
FIG. 6 is a graph depicting dehydration studies in THF with levoglucosan (■) and glucose (●) feedstocks under acidic conditions at 170° C. Relative HMF carbon selectivity as a function of total carbon yield of detectable products is presented. Feedstock loading was 2 wt % and reaction volume was 60 mL. Catalyst concentration was 5 mM sulfuric acid.
Figures 7A, 7B, 7C, 7D:
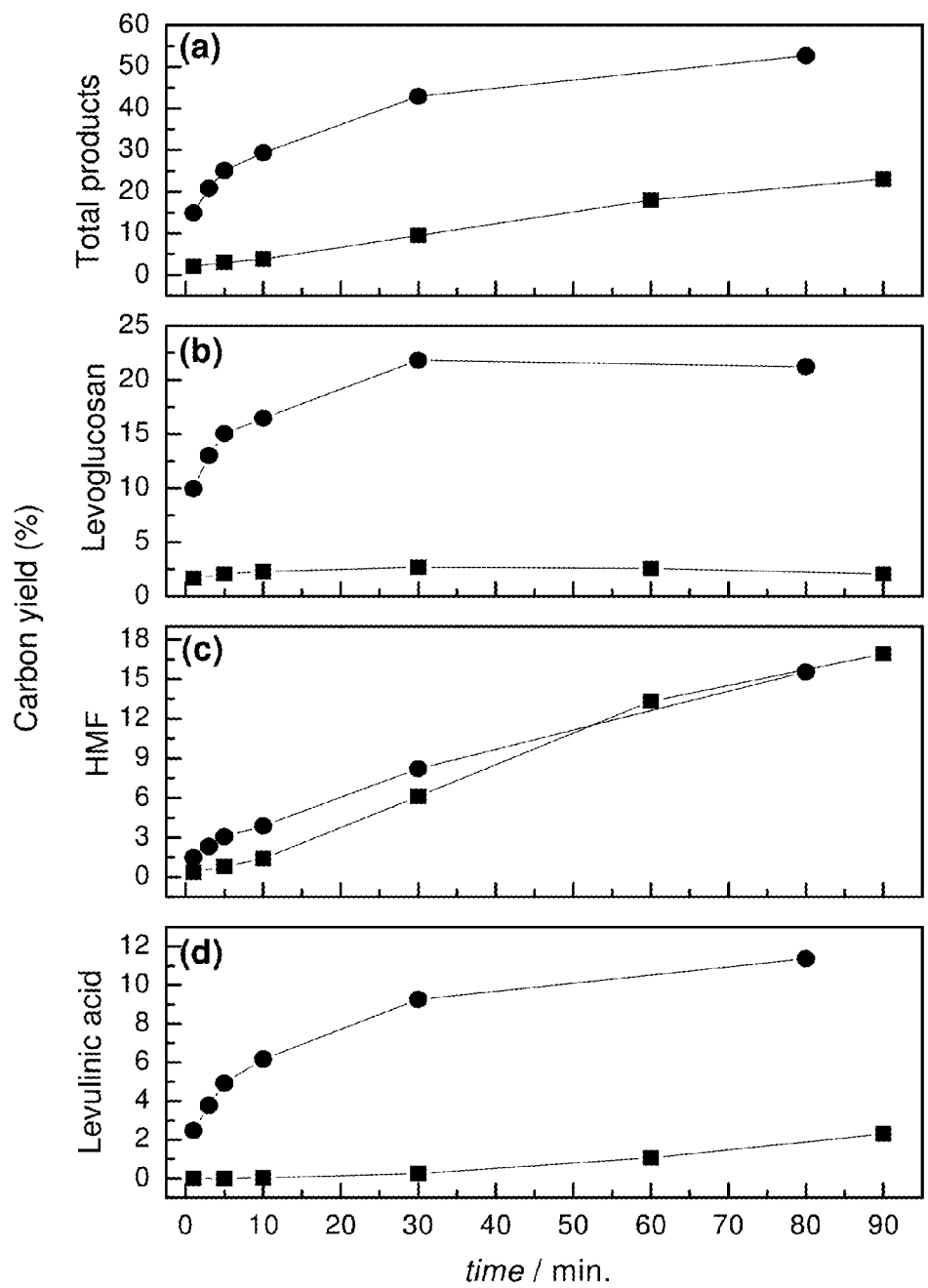
FIGS. 7A, 7B, 7C, and 7D are a series of graphs depicting the effect of solvent in glucose dehydration studies under acidic conditions at 170° C. The graphs depict carbon yields as a function of reaction time for various products.

THF was selected as the reaction solvent for more detailed studies. Biphasic mixtures of THF and water have been used in a wide array of biomass conversion processes, including furfural production from hemicellulose, HMF production from glucose and the use of co-solvent systems to produce the aforementioned products from maple wood.[26a] Cellulose decomposition with dilute sulfuric acid was carried out in four different solvent systems (pure THF, pure water, a 1:1 THF/water mixture, and a 9:1 THF/water mixture), as shown in FIGS. 3A, 3B, 3C, and 3D. Cellulose loading was 5 wt % and reaction volume was 60 mL. Catalyst concentration was 5 mM sulfuric acid. The major products detected were levoglucosan (FIG. 3A), glucose (FIG. 3B), HMF (FIG. 3C), and levulinic acid (FIG. 3D). Higher carbon yields of levoglucosan (7% after 60 minutes) were observed in pure THF compared to the other reaction mixtures. Levoglucosan is likely the primary decomposition product of cellulose in THF. Stoichiometry requires that water be a reactant for the production of glucose from cellulose.[32] Levoglucosan is also the major product from gas-phase cellulose pyrolysis.[33] Glucose is observed when THF is the reaction solvent. Separate experiments with levoglucosan in THF under acidic conditions confirmed that HMF and levulinic acid can be produced directly from levoglucosan. See the Examples and FIGS. 5A, 5B, and 5C. The HMF and levulinic acid yields were higher when glucose was used as a feedstock compared to levoglucosan. However, the relative HMF carbon selectivity was higher when levoglucosan was used as the feedstock. See the Examples and FIG. 6. Levoglucosan (21% after 30 minutes) was also observed as a product from glucose dehydration when THF was used as a solvent. See the Examples and FIGS. 7A, 7B, 7C, and 7D. In contrast, only trace levels of levoglucosan were observed when water was used as a solvent for glucose dehydration.

Figure 8:
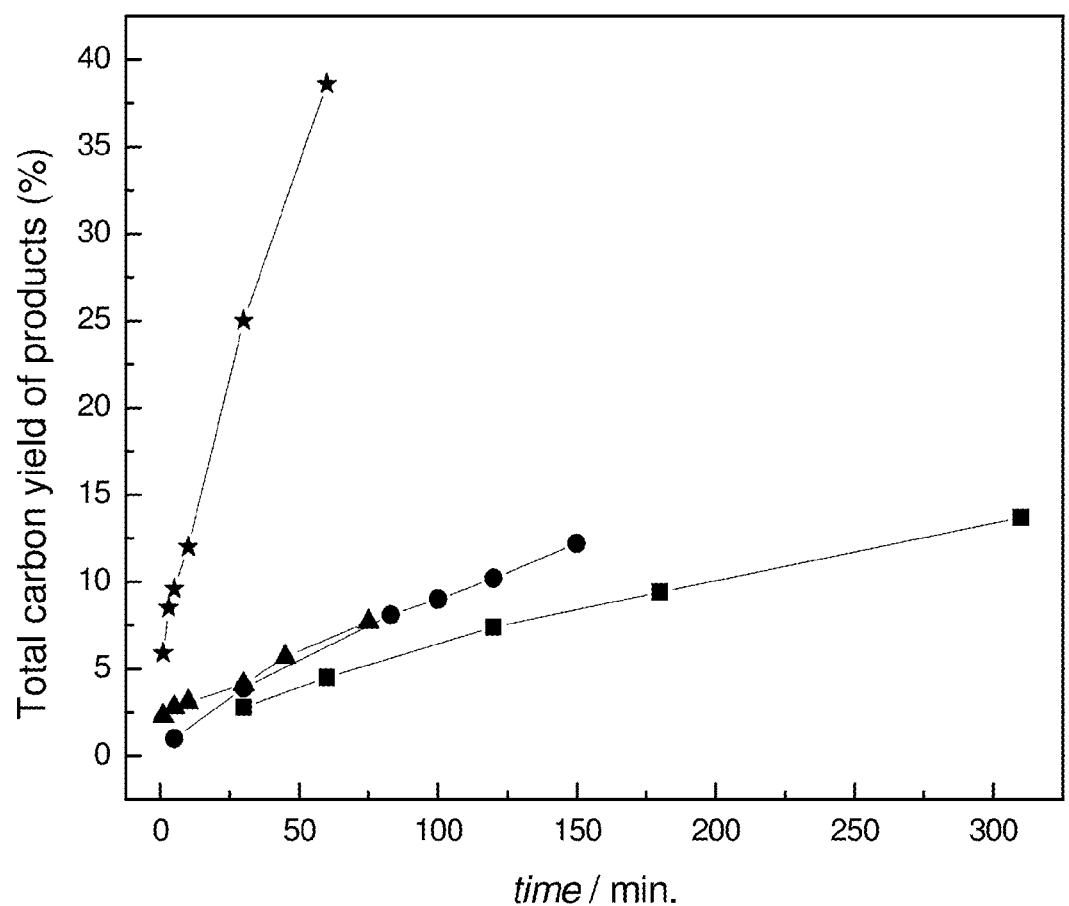
FIG. 8 is a graph depicting cellulose decomposition in THF/water mixtures under acidic conditions. The graph depicts total carbon yield of detectable products as a function of reaction time at 170° C. Cellulose loading was 5 wt % and reaction volume was 60 mL. Catalyst concentration was 5 mM sulfuric acid. Water (■), water:THF 1:1 v/v (●), water:THF 1:9 v/v (▲), THF (★).
Figure 9:
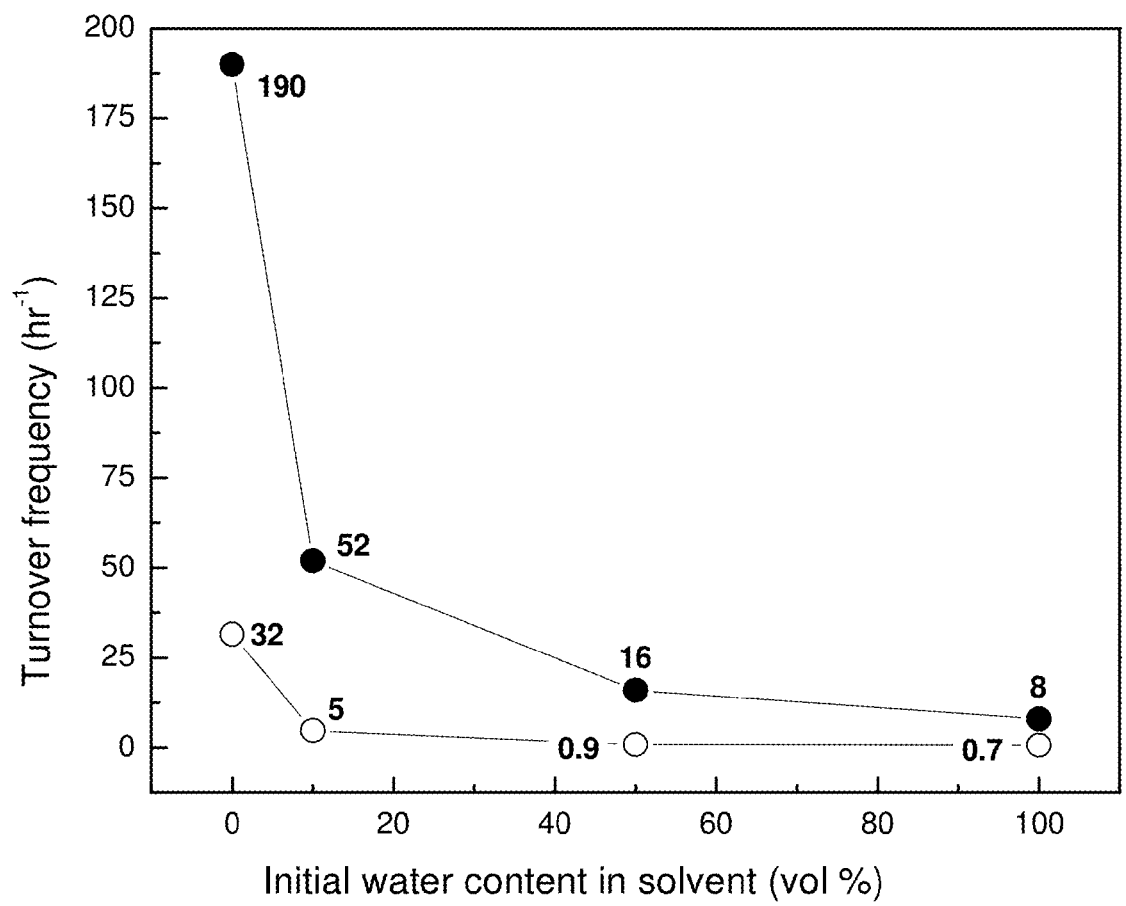
FIG. 9 is a graph depicting cellulose decomposition in THF/water mixtures under acidic conditions. Depicted in the graph is initial turnover frequency (based on the total moles of carbon from the detectable products) as a function of initial water content in solvent at 170° C. Cellulose loading was 5 wt % and reaction volume was 60 mL. Catalyst concentration was 5 mM sulfuric acid.

The carbon yields of HMF and levulinic acid increased as the water content in the solvent decreased. See FIGS. 3C and 3D. The initial turnover frequency (TOF) for cellulose conversion per sulfuric acid site was calculated from the data in FIG. 8. The TOF in THF was more than twenty fold higher than the TOF in pure water. See FIG. 9. It is possible that this proportion may be overestimated to some extent because a fraction of the cellulose converted (~50%) can also produce insoluble humins in pure water. Nevertheless, the water has a significant inhibition effect on cellulose decomposition, as well as the dehydration reactions. It is believed that the acid sites are less reactive in the presence of water due to solvation of the proton by water molecules. For example, the Gibbs free energy for solvation of a proton changes from −265.9 kcal/mol in liquid water to −260.2 kcal/mol in an aprotic solvent such as acetonitrile.[35] Thus, the proton catalyst is stabilized in an aprotic solvent to a less extent than in water (by 5.7 kcal/mol), leading to higher reactivity of the proton, provided that the solvent has a more moderate effect on the transition state for the acid-catalyzed reaction relative to the reactant. This higher reactivity of the Brønsted acid catalyst in an aprotic solvent allows for the use of low acid concentrations to carry out the reaction. The TOF decreases from 190 hr$^{-1}$ to 52 hr$^{-1}$ as the solvent changes from 0% $H_2O$ to 10% $H_2O$. Minimizing the water concentration in the reactor leads to a number of advantages: (1) enhanced rate of furfural/HMF production from monosaccharides; (2) facilitated product recovery; (3) mitigation of degradation reactions, and (4) opportunity to use solid catalysts with improved stability in the reaction media.

Figure 4A:
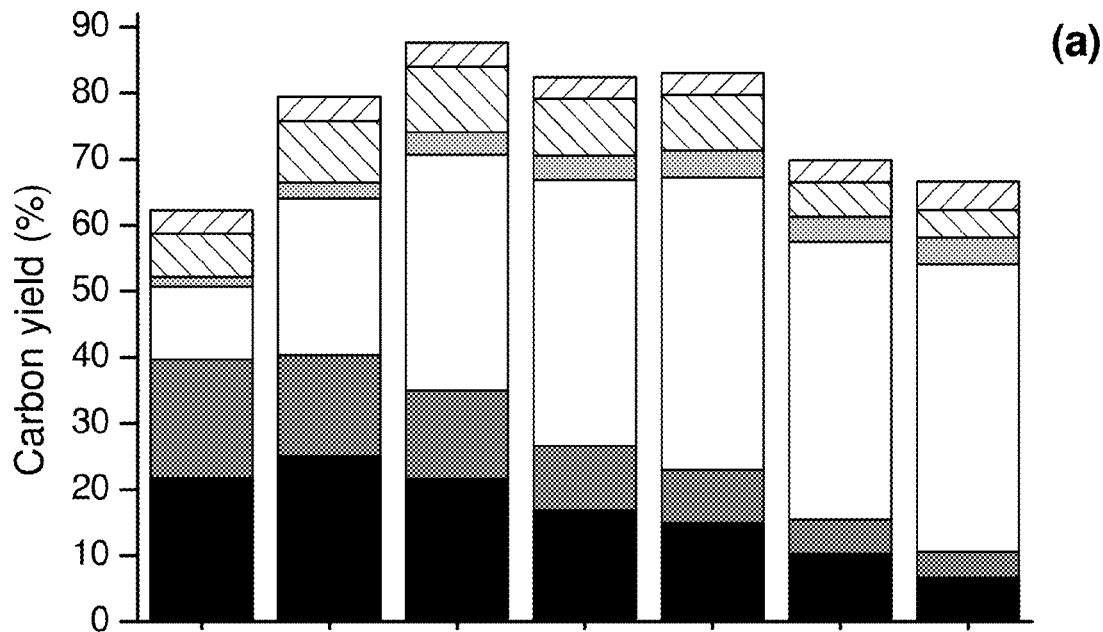
FIGS. 4A and 4B are a pair of graphs depicting cellulose decomposition in THF under acidic conditions at 190° C.
Figure 4B:
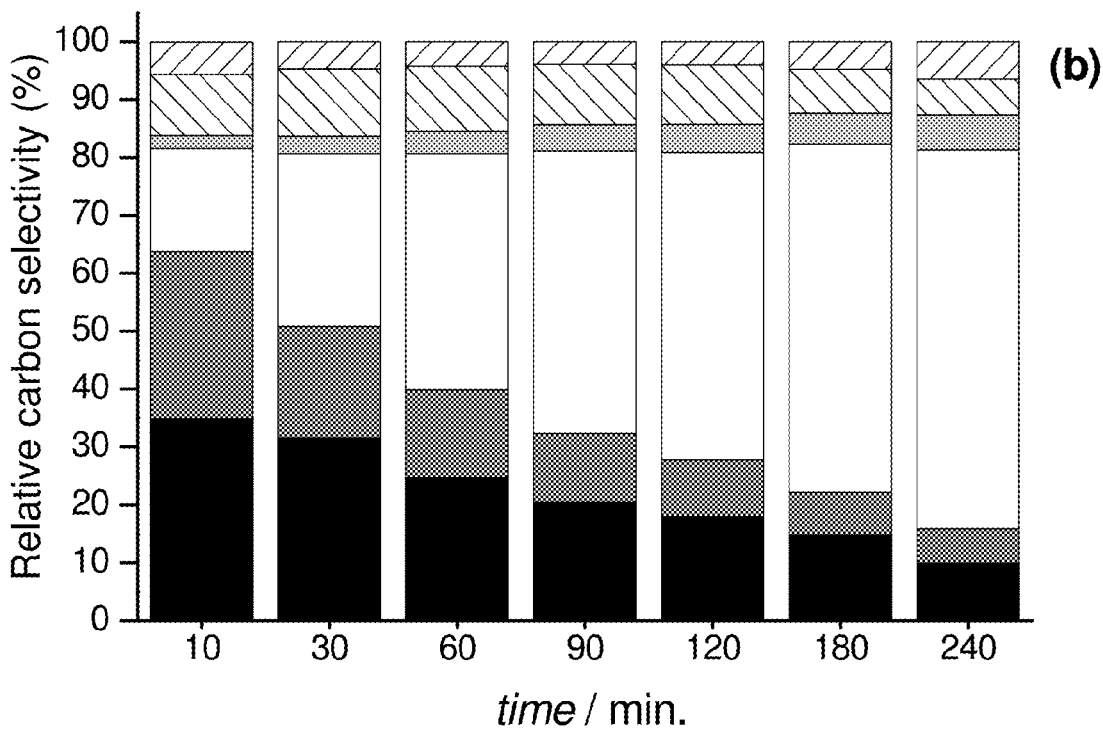
Figures 10A, 10B, 10C, 10D:
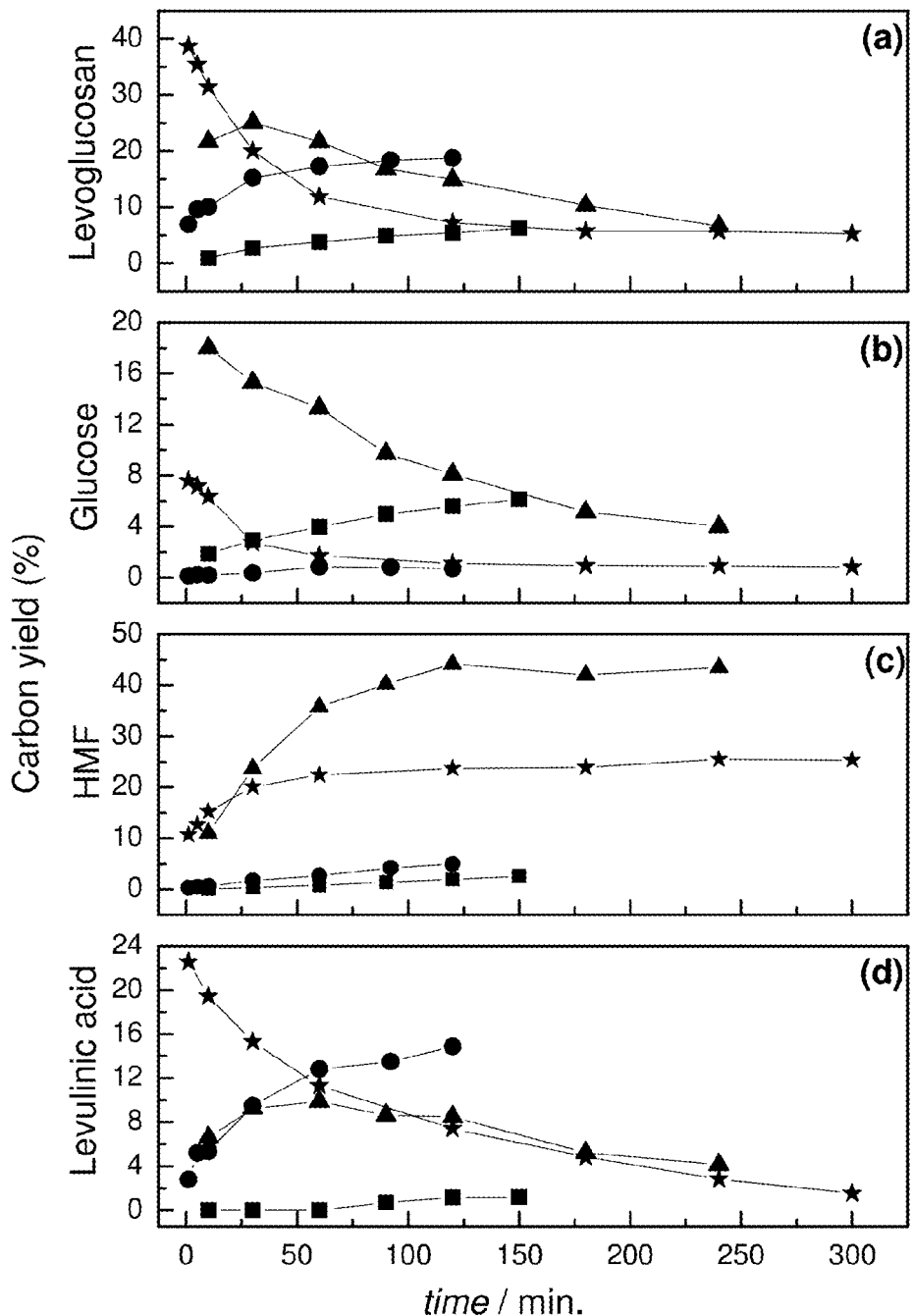
FIGS. 10A, 10B, 10C, and 10D are a series of graphs depicting the effect of temperature on cellulose decomposition in THF under acidic conditions. Each graph depicts the carbon yield of a major product as a function of reaction time at 170° C.

The product selectivity can be modified by adjusting the reaction temperature. The levoglucosan yield increased with increasing temperature as shown in FIGS. 10A-10D (FIG. 10B specifically) (39% yield after 1 minute at 210° C.). The HMF yield went through a maximum at 190° C. (FIG. 10C). FIGS. 4A and 4B show the carbon yield of all the detectable products and their relative carbon selectivity at 190° C. The HMF yield increased steadily with time reaching 44% after 120 minutes at 190° C. (FIG. 4A). The HMF yield then remained constant, even after 4 hours indicating that HMF does not undergo further degradation reactions. At 190° C. levoglucosan went through a maximum yield of 25% after 30 minutes. The glucose yield (18% maximum) decreased with reaction time at 190 and 210° C. The cumulative detectable products carbon yield at 190° C. went through a maximum of 88% after 60 minutes, decreasing to 67% after 4 hours, suggesting that undesired humins form in this reaction. The stable HMF yield suggests that levoglucosan and glucose are the major source of humins formation at these reaction conditions. The concentration of water produced under these reaction conditions can reach up to 0.2 wt % in THF with quantitative yields of HMF (assuming water is only produced via dehydration reactions and water is only consumed via rehydration to produce levulinic acid). Accordingly, based on the data in FIGS. 4A and 4B, the water concentration after 120 minutes is 0.08 wt %. Consequently, removing water from the reaction system could further suppress side reactions and improve HMF selectivity.

The method thus provides a straightforward route to convert cellulose into HMF in polar aprotic solvents (i.e., THF) under dilute acid conditions. In this sequence of reactions, levoglucosan is the first major decomposition product of cellulose, followed by dehydration to produce HMF. Glucose, levulinic acid and formic acid are products from side reactions with water, which is a by-product of dehydration. The maximum obtainable yield of HMF achieved in the Examples was 44%, with a combined yield of 53% for HMF and levulinic acid. The method disclosed here has several distinct advantages compared to other existing processes to produce HMF from cellulose, including a 20× reduction in acid usage, a 20× higher reaction rate (compared to aqueous systems), the potential to use less expensive feedstocks (lignocellulosic biomass), operation at lower reaction temperatures, and improved stability of the HMF product in the solvent. Furthermore, the reactants and products can be separated from the solvent using conventional petrochemical separation technology. The method does not require using Lewis acids to promote isomerization of glucose to fructose as a preliminary step to produce HMF.

EXAMPLES

Reaction Studies:

Batch reactions were carried out in a 100 mL reactor vessel provided by Parr Instrument Company (Moline, Ill.), series 4560. The feedstock solutions were prepared with THF (Sigma-Aldrich, anhydrous, 99.9%, inhibitor free) at the specified concentrations. Microcrystalline cellulose (Avicel® PH-101, FMC Biopolymer, Philadelphia, Pa.) with a particle size of approximately 50 µm was provided by Sigma-Aldrich and used as received. Sulfuric acid (A300-500) and glucose were provided by Fisher Scientific (Waltham, Mass.). Levoglucosan (99%) and HMF (99%) were provided by Sigma-Aldrich. Throughout all of the experiments, the reaction volume was kept constant at 60 mL. Temperatures in the reactor were measured by means of a thermocouple in contact with the solution. Time zero in the reaction was defined as the time when the reactor reached the desired temperature. All reaction solutions were mixed at a maximum constant rate of 600 rpm using an internal stirrer. The temperature and stirring were controlled by a 4848 Controller provided by Parr. The reaction vessel was initially purged with UHP helium (Airgas, Radnor Township, Pa.) five times at room temperature to remove any air from the vessel. The vessel was then heated to the desired reaction temperature and then pressurized to a final pressure of 1000 psig. Samples were taken periodically through a sampling port. The reactor was repressurized with helium after each sampling. Sample vials were cooled beforehand in dry ice to suppress evaporation of the solvent during sampling. The samples were immediately quenched in an ice water bath and filtered with a 0.2 µm syringe filter (IC Millex®-LG, part no. SLLGC13NL; EMD-Millipore, Billerica, Mass.). Samples were diluted with water prior to analysis. The dip tube was covered with a stainless steel woven wire cloth, mesh size 400×400 provided by Grainger. This was done to prevent clogging and loss of feed during sampling.

Analysis:

Reaction product samples were analyzed by high pressure liquid chromatography (HPLC) with a Shimadzu© LC-20AD (Shimadzu Scientific Instruments, Inc., Columbia, Md.). Carbohydrates were detected with a RI detector (RID-10A). Formic acid, levulinic acid, furfural and HMF were detected with a UV-Vis detector (SPD-M20A) at wavelengths of 207, 207, 240 and 310 nm respectively. The column used was a Biorad© Aminex HPX-87H sugar column. The mobile phase was 0.005 M $H_2SO_4$ flowing at a rate of 0.6 mL/min. The column oven was set to 30° C.

REFERENCES CITED

[1] S. Dutta, S. De, B. Saha, *ChemPlusChem* 2012, 77, 259-272.
[2] (a) Y. Roman-Leshkov, C. J. Barrett, Z. Y. Liu, J. A. Dumesic, *Nature* 2007, 447, 982-985; (b) J. Jae, W. Zheng, R. F. Lobo, D. G. Vlachos, *ChemSusChem* 2013, 6, 1158-1162.
[3] (a) C. L. Williams, C.-C. Chang, D. Phuong, N. Nikbin, S. Caratzoulas, D. G. Vlachos, R. F. Lobo, W. Fan, P. J. Dauenhauer, *Acs Catalysis* 2012, 2, 935-939; (b) D. Wang, C. M. Osmundsen, E. Taarning, J. A. Dumesic, *Chemcatchem* 2013, 5, 2044-2050; (c) T. A. Brandvold, UOP LLC, US, 2012.
[4] R. Alamillo, M. Tucker, M. Chia, Y. Pagan-Tones, J. Dumesic, *Green Chem.* 2012, 14, 1413-1419.
[5] J. C. Shen, C. E. Wyman, *Aiche J.* 2012, 58, 236-246.
[6] (a) P. Daorattanachai, S. Namuangruk, N. Viriya-empikul, N. Laosiripojana, K. Faungnawakij, *Journal of Industrial and Engineering Chemistry* 2012, 18, 1893-1901; (b) S. D. Yin, Y. L. Pan, Z. C. Tan, *Int. J. Green Energy* 2011, 8, 234-247.
[7] S. Van de Vyver, J. Thomas, J. Geboers, S. Keyzer, M. Smet, W. Dehaen, P. A. Jacobs, B. F. Sels, *Energy Environ. Sci.* 2011, 4, 3601-3610.
[8] C. Li, Z. K. Zhao, A. Wang, M. Zheng, T. Zhang, *Carbohydr. Res.* 2010, 345, 1846-1850.
[9] J. B. Binder, R. T. Raines, *J. Am. Chem. Soc.* 2009, 131, 1979-1985.
[10] R. Rinaldi, R. Palkovits, F. Schuth, *Angewandte Chemie-International Edition* 2008, 47, 8047-8050.
[11] (a) H. Zhao, J. E. Holladay, H. Brown, Z. C. Zhang, *Science* 2007, 316, 1597-1600; (b) Y. Su, H. M. Brown, X. Huang, X.-d. Zhou, J. E. Amonette, Z. C. Zhang, *Applied Catalysis A: General* 2009, 361, 117-122.
[12] R. J. van Putten, J. C. van der Waal, E. de Jong, C. B. Rasrendra, H. J. Heeres, J. G. de Vries, *Chem. Rev.* 2013, 113, 1499-1597.
[13] S. M. Sen, J. B. Binder, R. T. Raines, C. T. Maravelias, *Biofuels, Bioproducts and Biorefining* 2012, 6, 444-452.
[14] R. Rinaldi, F. Schuth, *ChemSusChem* 2009, 2, 1096-1107.
[15] (a) M. E. Zakrzewska, E. Bogel-Lukasik, R. Bogel-Lukasik, *Chem. Rev.* 2011, 111, 397-417; (b) S. S. Y. Tan, D. R. MacFarlane, in *Ionic Liquids, Vol. 290* (Ed.: B. Kirchner), Springer-Verlag Berlin, Berlin, 2009, pp. 311-339.
[16] Z. Zhang, W. Liu, H. Xie, Z. K. Zhao, *Molecules* 2011, 16, 8463-8474.
[17] (a) K. D. Vigier, A. Benguerba, J. Barrault, F. Jerome, *Green Chem.* 2012, 14, 285-289; (b) F. Liu, J. Barrault, K. D. Vigier, F. Jerome, *ChemSusChem* 2012, 5, 1223-1226.
[18] (a) Y. Roman-Leshkov, J. N. Chheda, J. A. Dumesic, *Science* 2006, 312, 1933-1937; (b) J. N. Chheda, Y. Roman-Leshkov, J. A. Dumesic, *Green Chem.* 2007, 9, 342-350.
[19] Y. Roman-Leshkov, J. A. Dumesic, *Topics in Catalysis* 2009, 52, 297-303.
[20] J. S. Luterbacher, J. M. Rand, D. M. Alonso, J. Han, J. T. Youngquist, C. T. Maravelias, B. F. Pfleger, J. A. Dumesic, *Science* 2014, 343, 277-280.
[21] X. Qi, M. Watanabe, T. M. Aida, R. L. S. Jr., *Cellulose* 2011, 18, 1327-1333.
[22] H. Kawamoto, W. Hatanaka, S. Saka, *Journal of Analytical and Applied Pyrolysis* 2003, 70, 303-313.
[23] S. Helle, N. M. Bennett, K. Lau, J. H. Matsui, S. J. B. Duff, *Carbohydr. Res.* 2007, 342, 2365-2370.
[24] X. Hu, L. Wu, Y. Wang, D. Mourant, C. Lievens, R. Gunawan, C.-Z. Li, *Green Chem.* 2012, 14, 3087-3098.
[25] E. I. Gürbüz, J. M. R. Gallo, D. M. Alonso, S. G. Wettstein, W. Y. Lim, J. A. Dumesic, *Angewandte Chemie-International Edition* 2013, 52, 1270-1274.
[26] (a) C. M. Cai, T. Zhang, R. Kumar, C. E. Wyman, *Green Chem.* 2013; (b) Y. Yang, C. W. Hu, M. M. Abu-Omar, *Green Chem.* 2012, 14, 509-513.
[27] (a) M. Bicker, J. Hirth, H. Vogel, *Green Chem.* 2003, 5, 280-284; (b) M. Bicker, D. Kaiser, L. Ott, H. Vogel, *Journal of Supercritical Fluids* 2005, 36, 118-126.
[28] (a) J. Q. Bond, D. M. Alonso, D. Wang, R. M. West, J. A. Dumesic, *Science* 2010, 327, 1110-1114; (b) S. G. Wettstein, D. M. Alonso, Y. X. Chong, J. A. Dumesic, *Energy Environ. Sci.* 2012, 5, 8199-8203; (c) S. G. Wettstein, J. Q. Bond, D. M. Alonso, H. N. Pham, A. K. Datye, J. A. Dumesic, *Applied Catalysis B-Environmental* 2012, 117, 321-329.
[29] D. M. Alonso, J. M. R. Gallo, M. A. Mellmer, S. G. Wettstein, J. A. Dumesic, *Catalysis Science & Technology* 2013, 3, 927-931.

[30] D. M. Alonso, S. G. Wettstein, M. A. Mellmer, E. I. Giirbiiz, J. A. Dumesic, *Energy Environ. Sci.* 2013, 6, 76-80.
[31] J. M. R. Gallo, D. M. Alonso, M. A. Mellmer, J. A. Dumesic, *Green Chem.* 2013, 15, 85-90.
[32] H. Kobayashi, M. Yabushita, T. Komanoya, K. Hara, I. Fujita, A. Fukuoka, *Acs Catalysis* 2013, 3, 581-587.
[33] Y. C. Lin, J. Cho, G. A. Tompsett, P. R. Westmoreland, G. W. Huber, *J. Phys. Chem. C* 2009, 113, 20097-20107.
[34] M. Ohara, A. Takagaki, S. Nishimura, K. Ebitani, *Applied Catalysis A: General* 2010, 383, 149-155.
[35] C. P. Kelly, C. J. Cramer, D. G. Truhlar, *J. Phys. Chem. B* 2007, 111, 408-422.
[36] D. M. Alonso, S. G. Wettstein, J. A. Dumesic, *Green Chem.* 2013, 15, 584-595.

What is claimed is:

1. A method to produce 5-hydroxymethylfurfural (HMF), the method comprising:
reacting a reactant comprising cellulose, lignocellulose, or a combination thereof, in a reaction mixture comprising a polar, aprotic solvent and an acid, and wherein the reaction mixture is initially substantially devoid of water, for a time, at a temperature, and at a hydrogen ion concentration wherein at least a portion of the cellulose or lignocellulose present in the reactant is converted to HMF.

2. The method of claim 1, wherein the acid is present in an amount to yield a hydrogen ion concentration in the reaction mixture of from about 5 mM to about 500 mM.

3. The method of claim 1, wherein the acid is present in an amount to yield a hydrogen ion concentration in the reaction mixture of from about 5 mM to about 100 mM.

4. The method of claim 1, wherein the acid is present in an amount to yield a hydrogen ion concentration in the reaction mixture of from about 5 mM to about 50 mM.

5. The method of claim 1, wherein the acid is a Brønsted-Lowry Acid.

6. The method of claim 1, wherein the acid is a mineral acid.

7. The method of claim 1, wherein the temperature is from about 80° C. to about 300° C.

8. The method of claim 1, wherein the temperature is from about 80° C. to about 250° C.

9. The method of claim 1, wherein the temperature is from about 80° C. to about 200° C.

10. The method of claim 1, wherein the temperature is from about 140° C. to about 190° C.

11. The method of claim 1, wherein the polar, aprotic solvent is selected from the group consisting of beta-, gamma-, and delta-lactones, hydrofurans, hydropyrans, and combinations thereof.

12. The method of claim 1, wherein the polar, aprotic solvent is selected from the group consisting of dichloromethane, tetrahydrofuran, ethylacetate, acetone, dimethylformamide, acetonitrile, dimethylsulfoxide, propylene carbonate, N-methyl-2-pyrrolidone, and hexamethylphosphoramide.

13. The method of claim 1, wherein the reaction mixture comprises no more than about 0.2 wt % water at any time during the reaction.

14. A method to produce 5-hydroxymethylfurfural (HMF), the method comprising:
reacting a reactant comprising cellulose, lignocellulose, or a combination thereof, in a reaction mixture comprising a polar, aprotic solvent and an acid, for a time, at a temperature, and at a hydrogen ion concentration wherein at least a portion of the cellulose or lignocellulose present in the reactant is converted to HMF;
and wherein the reaction mixture is initially substantially devoid of water; and
wherein the reaction mixture comprises no more than about 0.2 wt % water at any time during the reaction.

15. The method of claim 14, wherein the acid is present in an amount to yield a hydrogen ion concentration in the reaction mixture of from about 5 mM to about 500 mM.

16. The method of claim 14, wherein the acid is present in an amount to yield a hydrogen ion concentration in the reaction mixture of from about 5 mM to about 100 mM.

17. The method of claim 14, wherein the acid is present in an amount to yield a hydrogen ion concentration in the reaction mixture of from about 5 mM to about 50 mM.

18. The method of claim 14, wherein the acid is a Brønsted-Lowry acid.

19. The method of claim 14, wherein the acid is a mineral acid.

20. The method of claim 14, wherein the temperature is from about 80° C. to about 300° C.

21. The method of claim 14, wherein the temperature is from about 80° C. to about 250° C.

22. The method of claim 14, wherein the temperature is from about 80° C. to about 200° C.

23. The method of claim 14, wherein the temperature is from about 140° C. to about 190° C.

24. The method of claim 14, wherein the polar, aprotic solvent is selected from the group consisting of beta-, gamma-, and delta-lactones, hydrofurans, hydropyrans, and combinations thereof.

25. The method of claim 14, wherein the polar, aprotic solvent is selected from the group consisting of dichloromethane, tetrahydrofuran, ethylacetate, acetone, dimethylformamide, acetonitrile, dimethylsulfoxide, propylene carbonate, N-methyl-2-pyrrolidone, and hexamethylphosphoramide.

* * * * *